United States Patent
Fried

(10) Patent No.: US 10,463,361 B2
(45) Date of Patent: Nov. 5, 2019

(54) SELECTIVE LASER VAPORIZATION OF MATERIALS

(71) Applicant: Nathaniel M. Fried, Concord, NC (US)

(72) Inventor: Nathaniel M. Fried, Concord, NC (US)

(73) Assignee: THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 1431 days.

(21) Appl. No.: 13/941,839

(22) Filed: Jul. 15, 2013

(65) Prior Publication Data
US 2014/0018784 A1 Jan. 16, 2014

Related U.S. Application Data

(60) Provisional application No. 61/671,262, filed on Jul. 13, 2012.

(51) Int. Cl.
| | |
|---|---|
| A61B 18/18 | (2006.01) |
| A61B 17/04 | (2006.01) |
| A61B 18/22 | (2006.01) |
| A61B 18/00 | (2006.01) |

(52) U.S. Cl.
CPC .......... *A61B 17/0467* (2013.01); *A61B 18/22* (2013.01); *A61B 18/00* (2013.01); *A61B 2018/00625* (2013.01); *A61B 2018/00982* (2013.01); *A61B 2018/2266* (2013.01)

(58) Field of Classification Search
CPC ..... A61B 18/22; A61B 18/00; A61B 17/0467; A61B 2018/2266; A61B 2018/00625; A61B 2018/00982
USPC ......................................................... 606/11
See application file for complete search history.

(56) References Cited

U.S. PATENT DOCUMENTS

| | | | | |
|---|---|---|---|---|
| 5,234,006 | A * | 8/1993 | Eaton | A61B 17/06166 128/898 |
| 5,651,377 | A * | 7/1997 | O'Donnell, Jr. | A61B 17/06166 128/898 |
| 6,165,170 | A * | 12/2000 | Wynne | A61B 18/203 606/10 |
| 6,547,806 | B1 * | 4/2003 | Ding | A61B 17/0057 606/213 |

(Continued)

FOREIGN PATENT DOCUMENTS

WO WO 2011140282 A2 * 11/2011 ....... A61B 17/06166

OTHER PUBLICATIONS

Shein et al, "Selective Laser Suture Lysis with a Compact, Low-Cost, Red Diode Laser" Aug. 20-24, 2008.IEEE, p. 4358-4360 (Year: 2008).*

(Continued)

*Primary Examiner* — Gary Jackson
*Assistant Examiner* — Sebastian X Lukjan
(74) *Attorney, Agent, or Firm* — Oliff PLC; R. Brian Drozd

(57) ABSTRACT

A system may include a laser configured to output laser light with a wavelength between 600-780 nm, and a radiation delivery device. The radiation delivery device may be configured to output the laser light to a mesh or suture implant so that the mesh or suture implant is exposed to the laser light. The mesh or suture implant is attached to a patient and surrounded at least partially by tissue of the patient. The mesh or suture implant is vaporized by exposure to the laser light while tissue exposed to the laser light is not damaged by the laser light.

18 Claims, 7 Drawing Sheets

(56) References Cited

U.S. PATENT DOCUMENTS

| | | | | |
|---|---|---|---|---|
| 9,277,964 | B1* | 3/2016 | Hasling | A61B 5/02042 |
| 2004/0068267 | A1* | 4/2004 | Harvie | A61B 17/00491 |
| | | | | 606/92 |
| 2008/0077198 | A1* | 3/2008 | Webb | A61N 5/0618 |
| | | | | 607/88 |
| 2009/0326617 | A1* | 12/2009 | Asano | A61B 5/02007 |
| | | | | 607/89 |
| 2011/0196355 | A1* | 8/2011 | Mitchell | A61B 18/22 |
| | | | | 606/11 |

OTHER PUBLICATIONS

Iglesia et al.; "Vaginal Mesh for Prolapse;" A Randomized Controlled Trial; Obstetrics & Gynecology; American College of Obstetricians and Gynecologists; vol. 116, No. 2, Part 1; Aug. 2010.

Withagen et al.; "Trocar-Guided Mesh Compared With Conventional Vaginal Repair in Recurrent Prolapse;" a Randomized Controlled Trial; Obstetrics & Gynecology; American College of Obstetricians and Gynecologists; vol. 117, No. 2, Part 1; Feb. 2011.

Nieminen et al.; "Outcomes after anterior vaginal wall repair with mesh: a randomized, controlled trial with a 3 year follow-up;" Research Urogynecology; American Journal of Obstetrics & Gynecology; www.AJOG.org; Sep. 2010.

Rardin et al.; "New Considerations in the Use of Vaginal Mesh for Prolapse Repair;" The Journal of Minimally Invasive Gynecology; vol. 16, No. 3; May/Jun. 2009.

Miller et al.; "Prospective Clinical Assessment of the Transvaginal Mesh Technique for Treatment of Pelvic Organ Prolapse—5-Year Results;" Female Pelvic Medicine & Reconstructive Surgery; www.fpmrs.net; vol. 17, No. 3; May/Jun. 2011.

Foon et al.; "Adjuvant materials in anterior vaginal wall prolapse surgery: a systematic review of effectiveness and complications;" Int Urogynecol J; The International Urogynecological Association; vol. 19; pp. 1697-1706; Jul. 8, 2008.

Diwadkar et al.; "Complication and Reoperation Rates After Apical Vaginal Prolapse Surgical Repair;" Obstetrics & Gynecology; vol. 113, No. 2, Part 1; Feb. 2009.

Barber; "Surgical Techniques for Removing Problematic Mesh;" Clinical Obstetrics and Gynecology; vol. 56, No. 2; pp. 289-302; Jun. 2013.

Blanchet et al.; "Laser ablation: Selective unzipping of addition polymers;" Appl. Phys. Lett.; vol. 68, No. 7; American Institute of Physics; Feb. 12, 1996.

Dillon et al.; "Management of two synthetic midurethral slings eroded into the urethral lumen;" Int Urogynecol J; The International Urogynecological Association; Oct. 6, 2012.

Feiner et al.; "Removal of an Eroded Transobturator Tape from the Bladder Using Laser Cystolithotripsy and Cystoscopic Resection;" Urology; vol. 73; pp. 681.e15-681.e16; 2009.

Davis et al.; "Evaluation of endoscopic laser excision of polypropylene mesh/sutures following anti-incontinence procedures;" Department of Urology, Mid-Western Regional Hospital, Dooradoyle, Limerick, Ireland; Nov. 2012.

Johnson et al.; "Antegrade Endoscopic Removal of Retained Urethral Sling Mesh in the Bladder;" Journal of Endourology; vol. 26, No. 8; Division of Urologic Surgery, Washington University School of Medicine; St. Louis, Missouri; Aug. 8, 2012.

Zakri et al.; "Intravesical Tension-Free Vaginal Tape Removal: Is There a Single Solution?;" International Scholarly Research Network; ISRN Urology; vol. 2011; Article ID 343850; 2011.

Lawrentschuk et al.; "Use of holmium laser for removal of an intraluminal ureteric suture;" International Journal of Urology; vol. 11; pp. 916-918; 2004.

Burks et al.; "Selective Laser Vaporization of Polypropylene Mesh Used in Treatment of Female Stress Urinary Incontinence and Pelvic Organ Prolapse: Preliminary Studies Using a Red Diode Laser;" Lasers in Surgery and Medicine; Wiley Periodicals, Inc.; vol. 44: pp. 325-329; Mar. 16, 2012.

\* cited by examiner

SELECTIVE LASER VAPORIZATION OF MATERIALS

CROSS-REFERENCE TO RELATED APPLICATIONS

The present application is a non-provisional application claiming the benefit of priority under 35 U.S.C. 119(e) to U.S. Provisional Patent Application No. 61/671,262, filed on Jul. 13, 2012 and entitled SELECTIVE LASER VAPORIZATION OF MATERIALS, which is hereby incorporated in its entirety.

FIELD

Embodiments of the present invention relate to methods and devices to vaporize materials. More specifically, embodiments of the invention comprise methods and devices to selectively vaporize mesh materials and sutures within the body of a patient.

BACKGROUND

The most common mesh-related complication experienced by patients undergoing transvaginal polypropylene synthetic slings for stress urinary incontinence (SUI) and transvaginal pelvic organ prolapse (POP) repair with mesh is vaginal mesh erosion. More than half of the patients who experience erosion from synthetic mesh require surgical excision which is technically challenging and risks damage to healthy adjacent tissue.

Over 200,000 sling procedures for female stress urinary incontinence and pelvic organ prolapse are performed annually in the United States. Additionally, there are over 800,000 hernia repair procedures performed in the United States each year that use the same polypropylene (prolene) mesh and that suffer from very similar complications to that of the SUI and POP patients. During these procedures, a strength-bearing mesh material consisting of non-absorbable polypropylene is placed inside the body for muscle reinforcement. In a significant number of procedures (~10%), complications from the polypropylene mesh occur, including mesh erosion and dyspareunia. The mesh may be cut by a sharp instrument and realigned or removed during surgical revision. This process is tedious as it involves cutting the mesh scaffold from interwoven healthy tissue. However, damage is typically caused to such surrounding healthy tissue which causes an extensive recovery period and extra pain in the patient.

BRIEF SUMMARY

In one embodiment, a laser system may be used to selectively vaporize material including mesh material and sutures used in the body of a patient (i.e. a human or animal). The surrounding healthy tissue is unaffected while a specific area or wide area of mesh is selected to be cut by the laser.

In a further embodiment, a red diode laser is used to vaporize polypropylene (and other material) sutures and mesh strands without significant thermal damage to surrounding tissue.

In one aspect, a method to vaporize a mesh or suture material is provided. The mesh or suture material is attached to a patient and surrounded at least partially by tissue of the patient. A laser and a controllable lens may be provided. The laser is activated to output the laser light, and the controllable lens may be focused on the mesh or suture material so that the controllable lens focuses the laser light from the laser onto a portion of the mesh or suture material.

In another aspect, a method may include providing a laser configured to output laser light, and providing a radiation delivery device that is configured to receive the laser light from the laser. The laser is activated to output laser light having a wavelength between about 600 nm to 1300 nm to the radiation delivery device. The radiation delivery device is configured to output the laser light to a mesh so that the mesh is exposed to the laser light.

In yet another aspect, a system for vaporization of mesh or suture material is provided. The system may include a laser configured to output laser light with a wavelength between 600-1300 nm, and a radiation delivery device. The radiation delivery device may be configured to output the laser light to a mesh or suture implant so that the mesh or suture implant is exposed to the laser light, wherein the mesh or suture implant is attached to a patient and surrounded at least partially by tissue of the patient. The mesh or suture implant is vaporized by exposure to the laser light while tissue exposed to the laser light is not damaged (e.g., heated to a temperature higher than a predetermined threshold) by the laser light.

BRIEF DESCRIPTION OF THE DRAWINGS

Embodiments of the present invention are illustrated by way of example and not limited by the figures of the accompanying drawings, in which like references indicate similar elements and in which.

DETAILED DESCRIPTION

Figure 1:
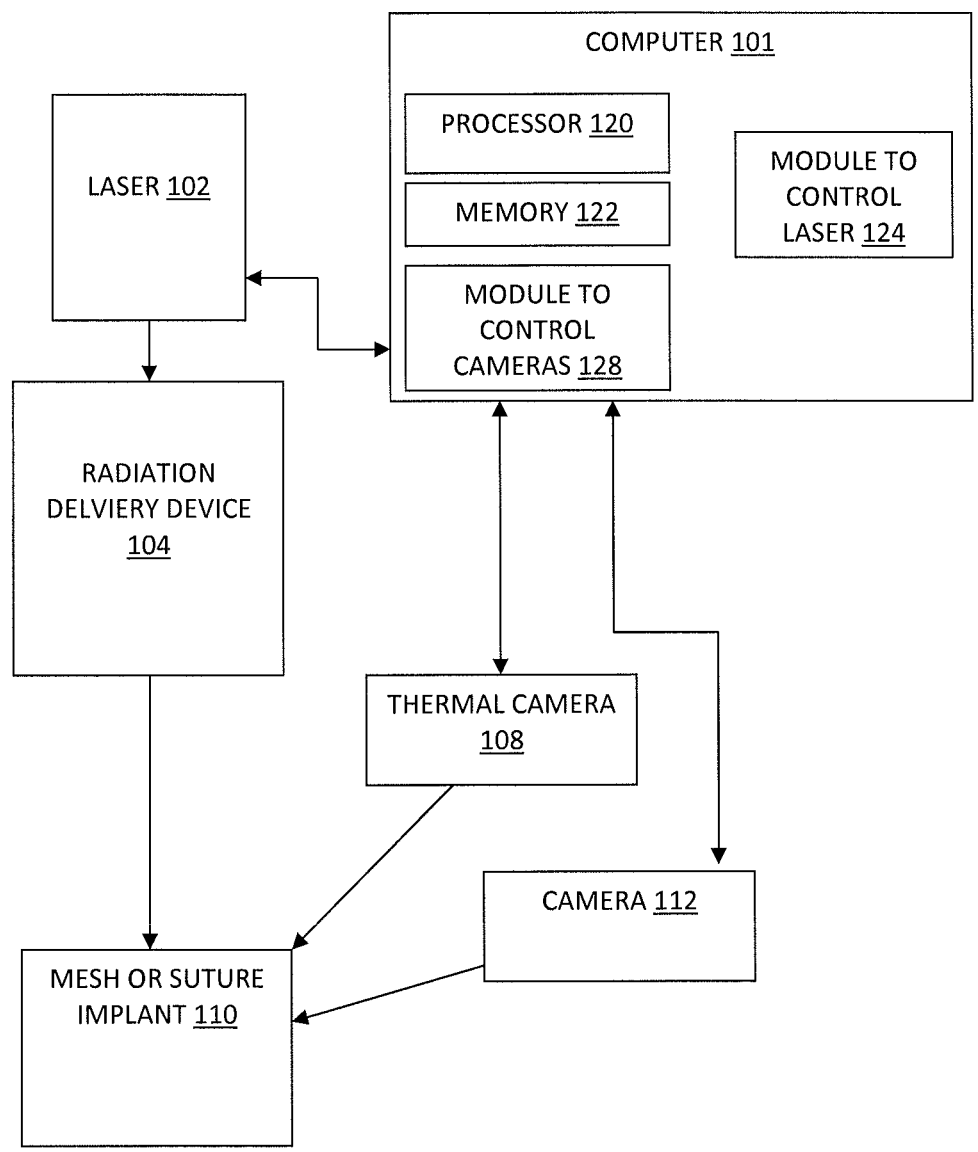
FIG. 1 illustrates an exemplary system for a laser vaporization of mesh materials according to one embodiment.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Devices and methods to vaporize materials such as mesh and sutures are described herein. In the following description, for purposes of explanation, numerous specific details are set forth in order to provide a understanding of embodiments of the present invention. It will be evident, however, to one skilled in the art that the present invention may be practiced with or without at least some of these specific details.

As used herein the term "patient" may refer to animal/mammal including humans, cats, dogs, horses, etc. which may be typically seen by a medical provider such as a surgeon or a veterinarian.

As used herein the term "photoselective" may refer to light that is selectively absorbed more strongly by a sample material (e.g., mesh material, suture material, etc.) than surrounding tissue, and the mesh strand diameter is vaporized using a single laser pulse.

Embodiments of the present invention comprise methods and devices to vaporize materials such as mesh and sutures with laser radiation. In some embodiments, devices of the invention include: a radiation source (e.g., a laser such as a laser with a wavelength between 600-1300 nm), and a radiation delivery device comprising, for example, a lens system and/or an optical fiber (such as a 100-1000-micron-core silica fiber) and a means of attaching the optical fiber to said lens and wherein some of the components of the radiation delivery device may be disposable in nature. In some embodiments, a miniature articulated arm or series of mirrors may be used to deliver the radiation to a patient. In some further embodiments, embodiments of the invention comprise an endoscope configured to deliver radiation from a laser through a radiation delivery device to a location within the body of a patient.

Figure 2:
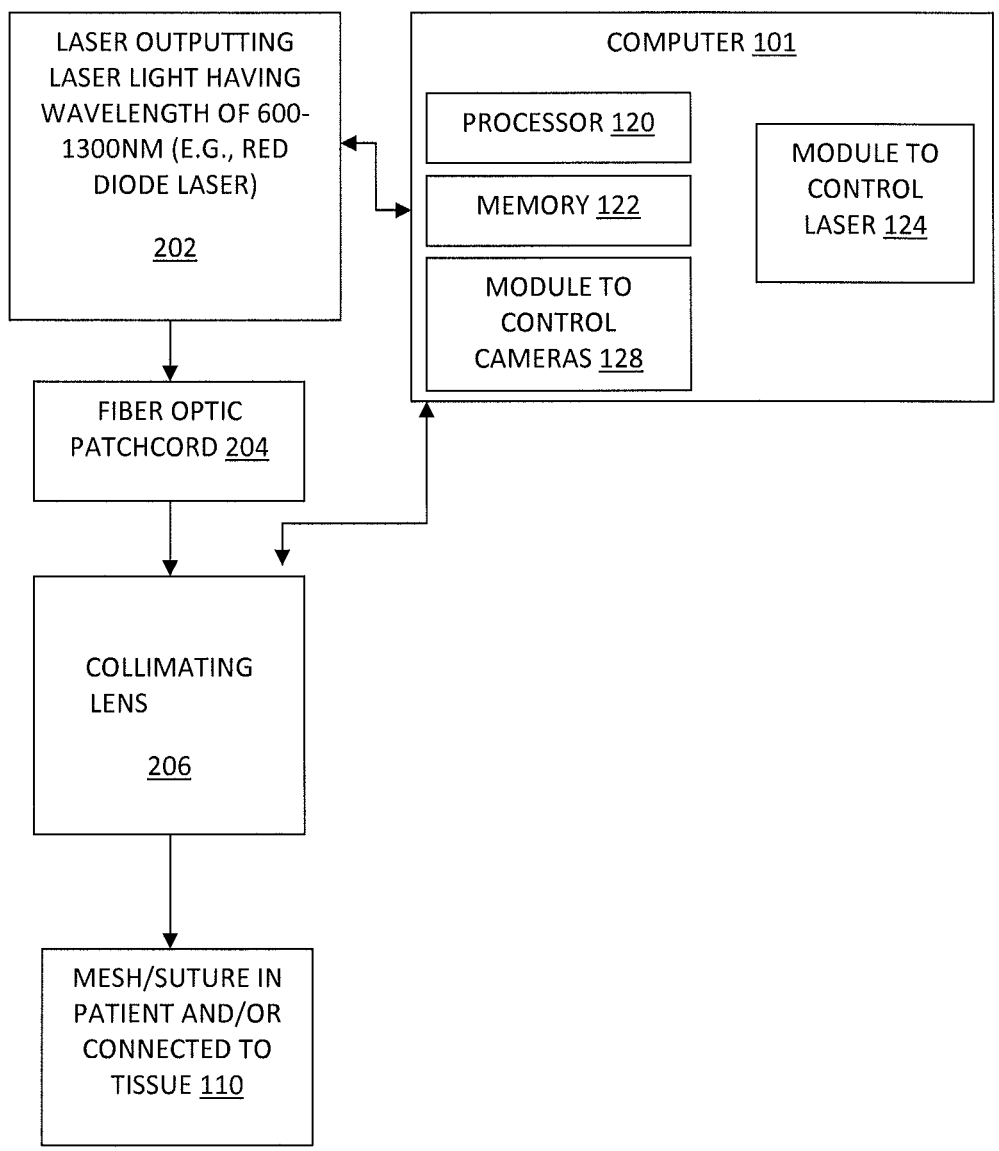
FIG. 2 illustrates another exemplary system for a laser vaporization of mesh materials according to another embodiment.

FIGS. 1-2 illustrate exemplary systems for a laser vaporization of mesh materials according to one embodiment. Referring first to FIG. 1, the system may include a computer 101, a laser 102, and a radiation delivery device 104. The system may further include (for surgical procedures or just experimental procedures) a thermal camera 108 and a camera 112 which may be controllable by the computer 101 or other control system. It should be understood that cameras 108 and 112 may not be employed in the system in a clinical setting as illustrated in FIG. 2.

The computer 101 may be a single computer or a series of computers. The computer 101 may be communicative with the devices in FIG. 1 (or FIG. 2) directly or over a network (not shown). The computer 101 may include a processor 120, memory 122, a module to control cameras 128, and a module to control laser 124. The processor 120 is configured to perform one or more of the operations of FIG. 3 discussed below. Additionally, the processor 120 may be configured to access computer instructions which may be stored in memory 122. The computer instructions may be called by the processor to perform one or more of the operations of FIG. 3.

The laser 102 may be configured to output laser light at a wavelength between 600 nm and 1300 nm. In one embodiment, the laser is configured to output laser light at a wavelength between 600 nm and 780 nm. In another embodiment, the laser is configured to output laser light at a wavelength at about 650 nm. The laser may be a red diode laser 202, as illustrated in FIG. 2.

In yet another embodiment, the laser is configured to output laser light at a wavelength between about 800-1300 nm, such as an infrared diode laser. In still yet another embodiment, the laser (e.g., InGaAs is configured to output laser light at a wavelength at about 904-1065 nm.

In this regard, it should be understood that the laser may be any type of laser configured to or capable of emitting laser light between 600 nm and 1300 nm (e.g., InGaAlP, InGaAs, Krypton, He—Ne, Alexandrite, Cr fluoride, GaAlAs, Ti: sapphire, Ruby, Nd:YAG, etc.). Therefore, a Krpyton laser which emits laser light at 647 nm may be used. Additionally, Helium Neon ("He—Ne") lasers which emit laser light at 594.1 nm, 611.9 nm, and/or 632.8 nm may be employed.

It should be understood that the term "red diode laser" may mean any laser which emits laser energy which is visible as a red light (e.g., between 600 nm-780 nm). However, it should be understood that lasers other than red diode lasers may also be employed. For example, an infrared laser that emits laser energy between 780 nm-1300 nm may also be employed, such as a neodymium-doped yttrium aluminum garnet (Nd: YAG) laser may be employed and emit laser energy with a wavelength of 946 nm or 1064 nm. In this regard, the suture material which may not normally absorb the laser light at these wavelengths may be coated with a preferential color dye, as discussed in more depth below with regard to FIG. 3.

It should be further understood that the present invention should not be limited to laser diode devices that are configured to output laser energy between 600-1300 nm. In fact, the present application is meant to include lasers which may produce laser light at a wavelength that is greater than 1300 nm or at a wavelength that is less than 600 nm. As mentioned below with regard to FIG. 3, dyes may be employed on the mesh or suture materials which would allow for lasers to be used that are outside of these ranges.

The laser 102 may be configured to pulse the laser light output ("pulsed mode") or provide continuous laser energy ("continuous mode"). A laser can be classified as operating in either continuous or pulsed mode, depending on whether the power output is essentially continuous or constant over time or whether its output takes the form of pulses of light on one or another time scale.

Pulsed operation of lasers refers to any laser not classified as continuous wave, so that the optical power appears in pulses of some duration at some repetition rate. Since the pulse energy is equal to the average power divided by the repetition rate, the laser energy can sometimes be increased by lowering the rate of pulses so that more energy can be built up in between pulses. In laser ablation, for example, a small volume of material at the surface of a work piece can be evaporated if it is heated in a very short time, whereas supplying the energy gradually would allow for the heat to be absorbed into the bulk of the piece, never attaining a sufficiently high temperature at a particular point. The optical bandwidth of a pulse may not be narrower than the reciprocal of the pulse width. In the case of extremely short pulses, that implies lasing over a considerable bandwidth, quite contrary to the very narrow bandwidths typical of continuous wave lasers. The lasing medium in some dye lasers and vibronic solid-state lasers produces optical gain over a wide bandwidth, making a laser possible which can thus generate pulses of light as short as a few femtoseconds (10-15 s).

The laser output is delivered to a mesh or suture material 110. The term "mesh or suture material" may refer to a mesh implant or a suture implant according to some embodiments. A mesh implant may include a plurality of legs or strands which are linked together to form a net-like structure about an area of tissue to hold the tissue together while the tissue heals to each other. The suture implant may be a series of single strands which each are individually used to hold adjacent tissues together. The suture may be a single strand which is worked through the tissue like laces to hold tissue together.

The radiation delivery device 104 may be a device connected with the laser 102 to assist in directing the laser light to the mesh/suture material. As illustrated in FIG. 2, the radiation delivery device 104 may include a fiber optic patchcord 204 and a collimating lens 206, as illustrated in the embodiment of FIG. 2. It should be noted that the radiation delivery device 104 may not include a lens and may simply be an output of the laser light to the mesh/suture.

A camera 112 may be employed to take pictures or videos of experiments of surgical procedures. Additionally, the camera 112 may be used to guide a surgeon to direct the light to the appropriate area to be vaporized. In this regard, the camera is used to magnify and align the laser beam with the suture/mesh.

A thermal camera 108 may be used to measure the temperature-time response of the laser irradiated tissue, suture, and/or mesh.

The module to control cameras 128 may be included in the computer 101 to control or receive data from camera 112 or thermal camera 108. In this regard, the computer 101 may have a video screen output to graphically provide the images from the cameras (108, 112) to a user or surgeon in real time.

The module to control the laser 124 may be implemented in a computer system integrated with the laser. The module to control the laser 124 may assist in varying the output wavelength of the laser so that the laser light is configured to output the laser light as predefined by the user.

Figure 3:
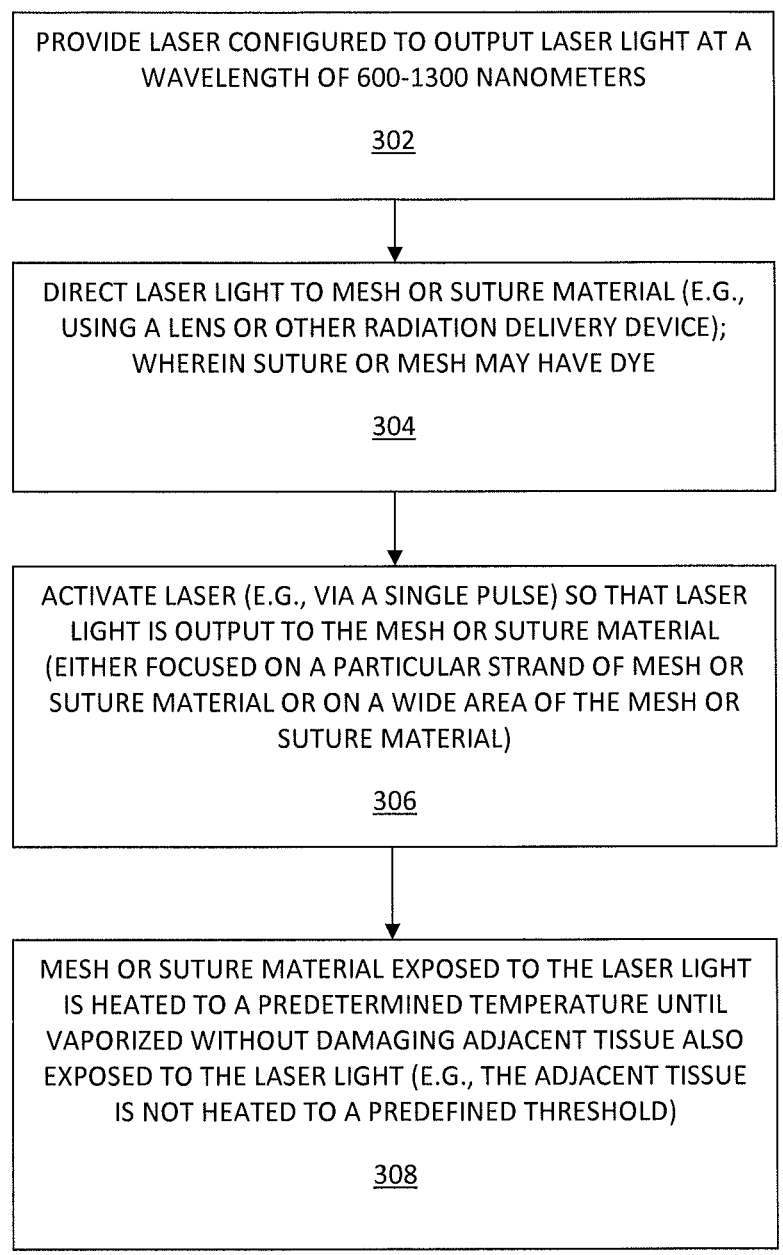
FIG. 3 illustrates a method for a laser vaporization of mesh materials according to one embodiment.

FIG. 3 illustrates a method for a laser vaporization of mesh materials according to one embodiment. In block 302, a laser, such as laser 102 or red diode laser 202, is provided. The laser may be configured to output laser light at 600 nm-1300 nm wavelength, as mentioned above.

Additionally, a mesh or suture implanted in a person or animal is provided. In one embodiment, the mesh may be manufactured with a preferential color or specially dyed to make laser vaporization easier or so that the laser light would be more readily absorbed directly to the mesh or suture material. This is because the dye would more readily absorb the laser energy light (and thus, heat) and transfer the absorbed heat directly to the mesh or suture material. In this regard, one could potentially use lasers outside the 600-780 nm wavelength range (e.g., between 780-1300 nm) to vaporized mesh or suture materials that are best suited to absorb laser energy at a wavelength between 600-780 nm. For example, black materials absorb light strongly not just in the visible, but also into the infrared as well, so one could stain the mesh or suture materials black in color instead of their current colors prior to implantation into the body of the patient, so that if the mesh or suture materials did need to be removed, one could then use an infrared laser beyond the 600-780 nm wavelength range to remove them.

In another embodiment, the mesh or suture materials are not dyed and instead are directly implanted into the patient. If the mesh or suture materials are polypropylene or nylon, these materials may preferentially be exposed to laser light at a wavelength between 600-780 nm. However, if the mesh or suture materials are polypropylene or nylon and were dyed with black dye color, the mesh or suture materials may preferentially be exposed to infrared wavelength light, such as between 780 nm-1300 nm.

In block 304, the radiation delivery device directs the laser light from the laser to the mesh or suture material implanted in a patient. It should be understood that the mesh or suture material may be made of nylon or polypropylene (which absorb laser light most effectively at wavelengths between 600 nm-780 nm). It should also be understood that the mesh or suture material may be any other implant material that may have strands and may be desired to be removed from a patient's tissue, including other implant material made of nylon or polypropylene. As such, the present invention should not be so limited to mesh or suture material.

Referring back to block 304, the laser light may be focused using a collimated lens 204. The collimated lens 204 may align and/or narrow the laser light to one particular leg or strand of the mesh implant or suture implant. In one embodiment, the lens (or another device) may direct the laser light to a large area of the mesh (or series of sutures) so that multiple legs of the mesh are simultaneously exposed to laser light (as well as adjacent surrounding tissue).

In block 306, the laser is activated so that laser light is output at 600 nm-780 nm by the laser. The laser light is output from the laser through the radiation delivery device (e.g., the lens) and to the mesh or suture material. The laser light may be pulsed. In one embodiment, a single pulse of the laser light is pulsed to the mesh or suture material, which vaporizes the mesh or suture material. In another embodiment, multiple pulses are continuously applied to the mesh or suture material.

In block 308, the mesh or suture material is exposed to the laser light and thus, absorbs the laser energy. The mesh or suture material heats itself up as a result of absorption of the laser energy. Once the mesh or suture material heats up to 180 degrees Celsius, the structure of the mesh or suture material is destroyed and at least a portion of the mesh or suture material is vaporized.

Because the laser light is pulsed and primarily absorbed by the mesh or suture material, the tissue is largely unaffected and a large area or complete mesh may be vaporized simultaneously using an unfocused or a wide laser beam. Thus, the mesh or suture material absorbs laser light at the same time adjacent tissue may be exposed to the laser light. However, the exposed tissue may not be damaged (e.g., the tissue is still healthy) while the exposed mesh or suture material is vaporized.

Experimental Example

The following experimental example is included to illustrate some embodiments of the present invention and some applications of the invention and should not be used to limit the scope of the claims.

Figure 4:
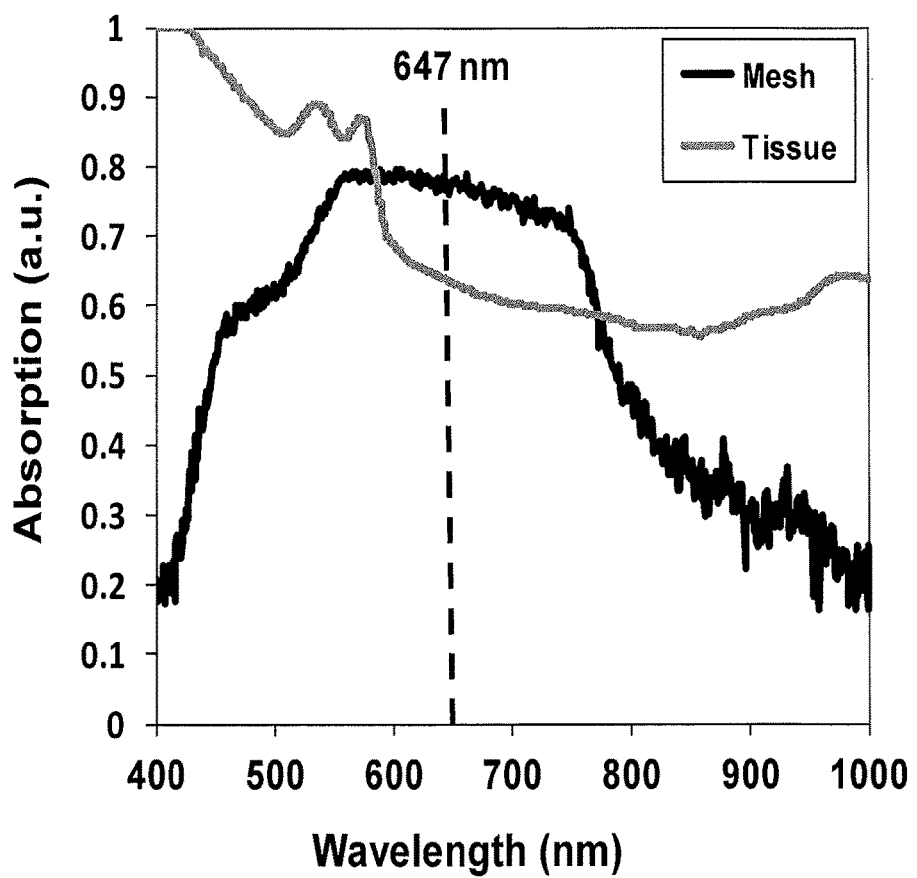
FIG. 4 shows absorption spectrum for polypropylene mesh and urinary tissue according to one embodiment.

In the example embodiment, laser energy is used to selective vaporize mesh or suture materials, including nylon and polypropylene, using a compact red diode laser. This method may be based on the principle of selective photothermolysis, which states that a structure (e.g. suture/mesh) can be destroyed through preferential absorption of pulsed laser radiation without thermal damage occurring to adjacent structures (e.g. tissue). As illustrated in FIG. 4, for selective laser vaporization of polypropylene mesh, there is a range of wavelengths in the red and infrared spectrum (600-780 nm) at which polypropylene mesh more strongly absorbs laser radiation than adjacent soft tissues, a condition desired for successful laser suture lysis. Outside this range, at shorter visible wavelengths hemoglobin is the dominant absorber in tissue, and at longer infrared wavelengths water is the dominant absorber in tissue.

In the experiment, samples of polypropylene 200-250 μm outer diameter sutures (3-0, Ethicon Blue Prolene Monofilament) and polypropylene mesh (TVT, Gynecare, Ethicon) were used as the mesh or suture materials. Fresh porcine ureteral tissue samples were obtained from the slaughterhouse for use as a simple soft urinary tissue model in these preliminary studies. The tissue samples were kept properly hydrated, placed on a thermally conductive plate in contact with a hotplate preset to a normal body temperature of 37° C. to simulate in vivo conditions. Either a single 3-0 polypropylene suture or a 1 cm×1 cm polypropylene mesh strip was placed in intimate contact with the tissue sample.

A compact, tabletop, 7 Watt, 647-nm, red diode laser (Model # ML2011, Modulight, Tampere, Finland) was provided as the laser. The red diode laser was operated with a radiant exposure of 81 J/cm$^2$ and pulse duration of 100 ms. A 400-μm-core silica fiber optic patch-cord was used to deliver the laser radiation from the laser to a lens collimating system, which provided a 0.95-mm-diameter collimated laser spot on the surface of the tissue sample (FIG. 2). A single laser pulse was delivered to the tissue, suture, or mesh sample in non-contact mode for each test. The laser parameters are summarized in Table 1.

TABLE 1

Summary of laser parameters used in laser vaporization of polypropylene suture/mesh:

| | |
|---|---|
| Wavelength | 647 |
| Radiant Exposure (J/cm$^2$) | 81 |
| Pulse Duration (milliseconds) | 100 |
| Spot diameter (mm) | 0.95 |
| Number of laser pulses | 1 |

A camera was used for magnification and alignment of the laser beam with the suture/mesh sample, and a thermal camera (e.g., A20M, Flir Systems, Billerica, Mass.) was used to measure the temperature-time response of the laser irradiated tissue, suture, or mesh sample during each test (FIG. 2).

Figure 5:
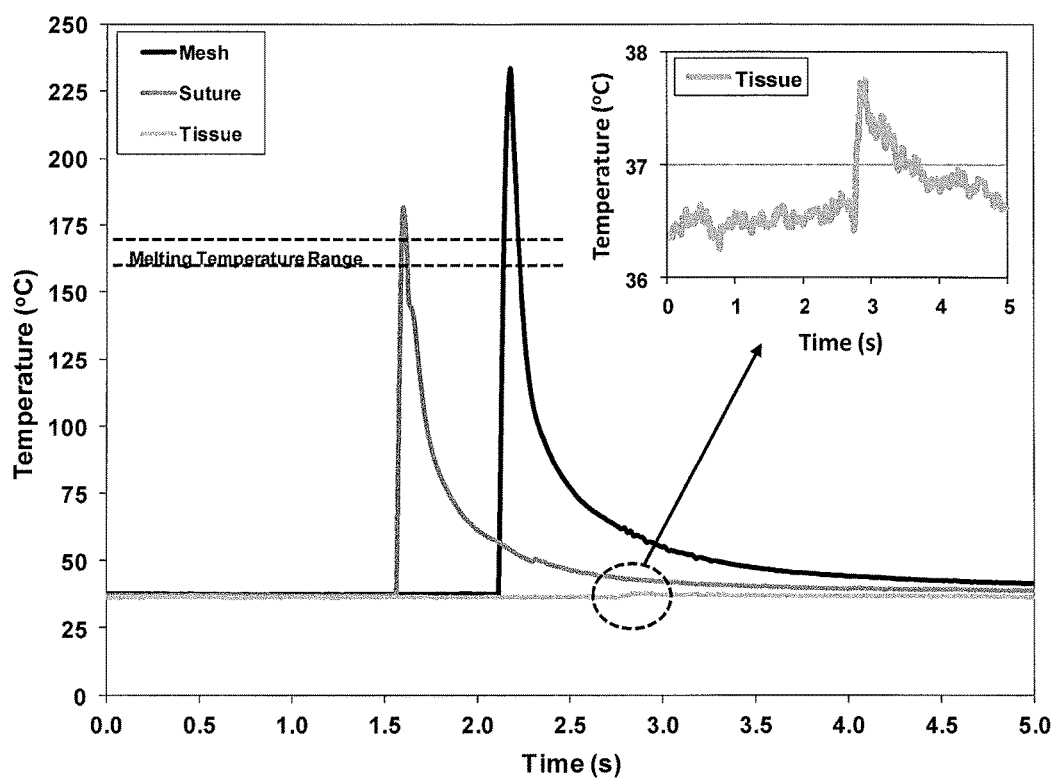
FIG. 5 shows temperature-time curves for the mesh materials during laser irradiation according to one embodiment.
Figure 6:
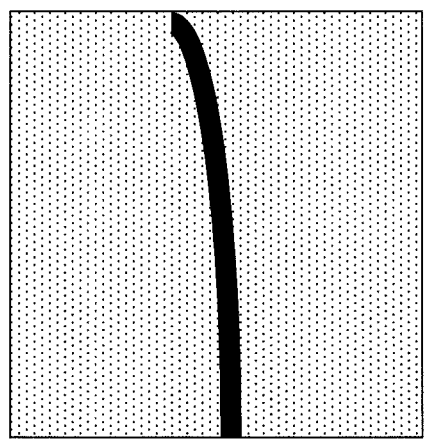
FIG. 6 illustrates a diagram of a polypropylene suture according to one embodiment.

A thermal camera was used for real-time, non-contact measurement of the peak temperatures achieved during laser irradiation of tissue, 3-0 polypropylene suture, and polypropylene mesh (FIG. 5). A negligible temperature increase of ~1° C., from 37° C. to 38° C. (n=10), was observed after a single laser pulse was delivered to soft urinary tissue alone. This study was performed to demonstrate that, due to the relative weak absorption of 647-nm laser radiation by soft tissue chromophores (e.g. hemoglobin and water), misalignment of the laser during a clinical procedure would not result in significant thermal elevation in the adjacent tissue.

As illustrated in FIG. 5, a large increase in temperature was observed when the single laser pulse irradiated both the polypropylene suture and mesh materials, resulting in peak temperatures of 180±13° C. (n=14) and 232±22° C. (n=28), respectively, in the polypropylene suture and mesh materials. The theoretical melting temperature of polypropylene is 171° C., with commercial products (e.g. sutures) having a melting point of 160-166° C. The melting temperatures of various polypropylene mesh configurations specifically used in SUI and POP procedures have been reported to be in the range of 154-172° C., with the melting temperature of this specific mesh type used in our study (e.g., TVT, Gynecare, Ethicon) was 169° C. Thus, the ablative temperatures reached in our studies were sufficient to exceed the melting temperature of polypropylene sutures and mesh, resulting in vaporization of the materials, as shown in Table 2:

TABLE 2

Summary of results for laser irradiation of tissue, suture, and mesh samples.

| | Tissue | Suture | Mesh |
|---|---|---|---|
| Initial temperature (° C.) | 36.7 +/− 0.6 | 37.0 +/− 0.8 | 37.8 +/− 1.2 |
| Peak temperature (° C.) | 37.7 +/− 0.4 | 180 +/− 13 | 232 +/− 22 |
| Change in temperature (° C.) | 1.0 | 143 | 194 |
| Melting temperature (° C.) | ~65 | 160-166 | ~169 |
| # samples (n) | 10 | 14 | 28 |

Figure 7:
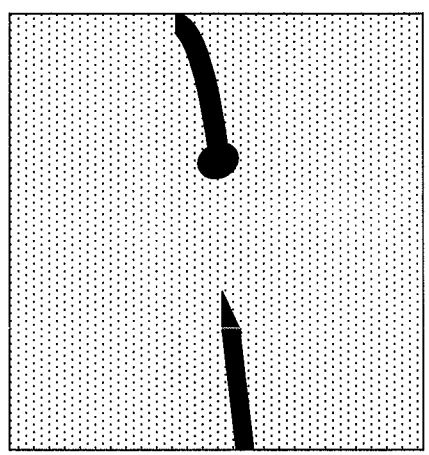
FIG. 7 illustrates a diagram of the polypropylene suture of FIG. 6 being ablated with the laser system of the present invention according to one embodiment.
Figure 8:
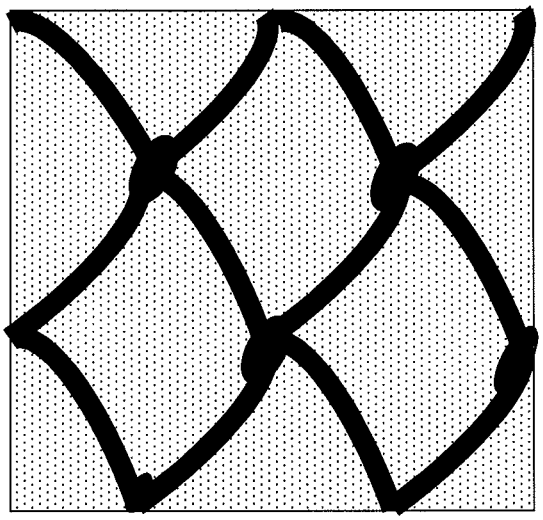
FIG. 8 illustrates a diagram of a polypropylene mesh according to one embodiment.
Figure 9:
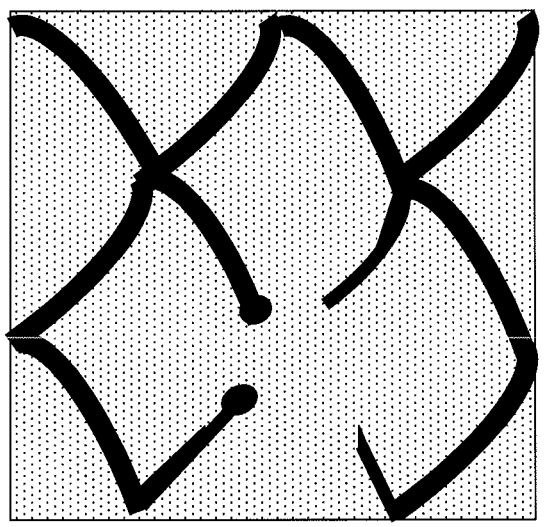
FIG. 9 illustrates a diagram of the polypropylene mesh of FIG. 8 being ablated with the laser system of the present invention according to one embodiment.

Representative images of the suture and mesh samples before and after single-pulse laser exposure are shown in FIGS. 6-9. FIG. 7 illustrates a diagram of the polypropylene suture of FIG. 6 being ablated with the laser system of the present invention according to one embodiment. FIG. 9 illustrates a diagram of the polypropylene mesh of FIG. 8 being ablated with the laser system of the present invention according to one embodiment. The polypropylene suture and mesh before and after laser vaporization methods. Note that even the thickest part of the mesh (e.g. the knot), can be vaporized. Residual mesh may be removed using successive laser pulses, if necessary Although some residue does exist after ablation, these fragments may be removed with application of successive laser pulses, if necessary.

Patients who undergo transvaginal synthetic slings for SUI repair and POP repair with mesh are subject to mesh-related complications. The most common mesh-related complication experienced by patients undergoing transvaginal POP repair with mesh is vaginal mesh erosion. Of the 10% of people who experience mesh erosion from SUI and POP repairs, more than half of them will need surgical excision in the operating room. Cutting, realignment, or removal of the mesh material may be necessary during surgical revision. This process may be tedious as it involves cutting the mesh scaffold from healthy tissue without causing damage to the ingrown tissue.

Treatment of polypropylene mesh exposure/erosion after SUI or POP repairs is challenging. Endoscopically, the Holmium:YAG laser has recently been used for treatment of intravesical polypropylene tape erosion after SUI procedures by vaporizing the mesh fragments. The Holmium laser was presumably chosen because of its availability in urology clinics where it is commonly available for use in lithotripsy and treatment of benign prostatic hyperplasia (BPH). However, the Holmium laser wavelength ($\lambda$=2120 nm) is not selectively absorbed by polypropylene or any other suture/mesh material, but rather couples strongly into the water component of tissues, thus risking thermal damage to surrounding tissue if the laser beam is misaligned.

Selective laser vaporization as discussed herein provides a safer and improved method of mesh removal. Unlike the argon blue-green light, the krypton red light is more selectively absorbed by the nylon suture material and only weakly absorbed by major tissue chromophores such as water and hemoglobin. However, argon and krypton lasers are gas lasers that are relatively large, expensive, and require significant maintenance. They have recently been replaced by more compact and less expensive solid-state, KTP ($\lambda$=532 nm) lasers and red diode lasers ($\lambda$=630-670 nm), respectively, for general use in laser medicine.

According to one embodiment of the present invention, a red diode laser (with similar 647-nm-wavelength to that of the krypton laser) can be used for selective vaporization of polypropylene suture and mesh materials, without any obvious indication of significant thermal insult to the adjacent tissue upon gross visual inspection. Due to selective absorption of red light by polypropylene it may also be possible in the future to automate the procedure by incorporating a scanning system into the fiber optic probe or handpiece so as to rapidly scan the laser spot across the entire mesh sample, for complete vaporization, in cases which warrant such an approach.

What is claimed is:

1. A method to vaporize a mesh or suture material, comprising
activating a laser to pulse a laser light beam having a wavelength between about 600 nm to 1300 nm to a collimating lens coupled with the laser, wherein the pulsing comprises applying the laser light beam to an area at a time period of less than or equal to a predetermined duration,
wherein the collimating lens is positioned to direct pulsing of the laser light beam to tissue and a portion of a mesh or suture material resulting in irradiation of both the tissue and the portion of the mesh or suture material, but the portion of the mesh or suture material is vaporized while the tissue remains healthy such that the laser light is directed on multiple legs of the mesh or suture material, thereby vaporizing the multiple legs of the mesh or suture material at the same time while tissue also exposed to the laser light is not damaged.

2. The method of claim 1, wherein the laser comprises one of a red diode laser or an infrared diode laser.

3. The method of claim 1, wherein the portion of the mesh or suture material comprises a portion of a surgical vaginal mesh implant that has been implanted into a vagina.

4. The method of claim 1, wherein the laser outputs a continuous-wave laser beam and the pulse is created by outputting the continuous-wave laser beam for a dwell time on a given area of suture/mesh/tissue, wherein the dwell time is equivalent to delivery of the laser energy in pulsed delivery mode.

5. The method of claim 1, wherein a portion of the mesh or suture material is separated from another portion of the mesh or suture material in response to a single pulse of the laser vaporizing the mesh or suture material.

6. The method of claim 1, wherein the output of the laser is only a single pulse to destroy the structure of the mesh or suture material without thermal damage occurring to adjacent tissue.

7. A method to vaporize a mesh or suture material comprising:
providing a laser configured to pulse laser light;
providing a collimating lens that is configured to receive the pulsed laser light from the laser;
activating the laser to pulse laser light at a wavelength of from 600 nm-1300 nm to the collimating lens, wherein the pulse comprises applying the laser beam to an area at a time period of less than or equal to a predetermined duration;
wherein, in response to the laser pulsing the laser light, the collimating lens irradiates the pulsed laser light to both a mesh or suture material and tissue, resulting in the mesh or suture material being vaporized without damaging the tissue so that the tissue remains healthy,
wherein the collimating lens allows the laser light to irradiate multiple legs of the mesh or suture material, thereby vaporizing the multiple legs of the mesh or suture material at the same time while tissue also exposed to the laser light is not damaged.

8. The method of claim 7, wherein the laser comprises a continuous-wave laser that outputs the laser light for less than or equal to a predetermined duration to generate the pulse.

9. The method of claim 8, further comprising dying the mesh or suture materials a predetermined color prior to the mesh or suture materials are implanted into the patient, and wherein the activating the laser comprises activating the laser to output a wavelength between 780 nm to 1300 nm.

10. The method of claim 7, wherein a single pulse of the laser destroys the structure of the mesh or suture material without thermal damage occurring to tissue adjacent to the mesh or suture material.

11. The method of claim 7, wherein the collimating lens is configured to be controlled to adjust a diameter of a beam of the laser light.

12. The method of claim 7, wherein the laser comprises a laser that is configured to output laser light at a wavelength between 600-780 nm.

13. A method to vaporize a mesh or suture material comprising:
activating a laser to pulse laser light with a wavelength between 600-1300 nm, wherein the pulse applies the laser light to an area at a time period of less than or equal to a predetermined duration,
wherein a collimating lens is coupled with the laser such that, while the laser is outputting the laser light at a wavelength between 600-780 nm, the collimating lens directs the pulsed laser light output by the laser to tissue and a mesh or suture implant so that the mesh or suture implant is vaporized by exposure to the laser light while tissue exposed to the laser light remains healthy when exposed to the laser light, wherein the portion of the mesh or suture material comprises a portion of a surgical vaginal mesh implant that has been implanted into a vagina.

14. The method of claim 13, wherein the laser is a red diode laser that is configured to output laser light with a wavelength between 600-780 nm.

15. The method of claim 13, wherein the collimating lens is configured to direct the laser light on only on one leg of the mesh or suture implant to only hit the laser light on the one leg using only a single pulse.

16. The method of claim 15, further comprising providing an optical fiber, and providing an attaching member that attaches the optical fiber to the lens.

17. The method of claim 15, wherein the collimating lens allows the laser light to irradiate multiple legs of the mesh or suture implant, thereby vaporizing the multiple legs of the mesh or suture implant at the same time while tissue also exposed to the laser light is not damaged.

18. The method of claim 7, wherein the portion of the mesh or suture material comprises a portion of a surgical vaginal mesh implant that has been implanted into a vagina.

\* \* \* \* \*